US00PP30446P3

(12) United States Plant Patent
Breach

(10) Patent No.: US PP30,446 P3
(45) Date of Patent: Apr. 30, 2019

(54) PEAR TREE NAMED 'NC4'

(50) Latin Name: *Pyrus communis*
Varietal Denomination: NC4

(71) Applicant: John Roland Breach, Staplehurst Tonbridge (GB)

(72) Inventor: John Roland Breach, Staplehurst Tonbridge (GB)

( * ) Notice: Subject to any disclaimer, the term of this patent is extended or adjusted under 35 U.S.C. 154(b) by 0 days.

(21) Appl. No.: 15/731,590

(22) Filed: Jul. 5, 2017

(65) Prior Publication Data

US 2018/0014441 P1 Jan. 11, 2018

Related U.S. Application Data

(60) Provisional application No. 62/493,553, filed on Jul. 8, 2016.

(51) Int. Cl.
*A01H 5/08* (2018.01)
*A01H 6/74* (2018.01)

(52) U.S. Cl.
USPC ..... Plt./176
CPC ..... *A01H 6/7481* (2018.05); *A01H 5/08* (2013.01)

(58) Field of Classification Search
USPC ..... Plt./176
CPC ..... A01H 5/0881
See application file for complete search history.

*Primary Examiner* — Kent L Bell
(74) *Attorney, Agent, or Firm* — Michelle Bos Legal LLC

(57) ABSTRACT

'NC4' is a new and distinct variety of pear tree (*Pyrus communis*), selected from seedlings produced as the result of a cross between female parent 'Concorde' (U.S. Plant Pat. No. 9,192) and male parent 'Red Williams' (not patented). 'NC4' is distinguished by its fruit, the skin overcolor of which is purple at harvest, turning to red and orange-red upon ripening.

8 Drawing Sheets

Latin name: *Pyrus communis.*
Variety denomination: 'NC4'.

BACKGROUND OF THE VARIETY

'NC4' is a new and distinct variety of pear tree (*Pyrus communis*), selected from seedlings produced as the result of a cross made in 2007 between female parent 'Concorde' (U.S. Plant Pat. No. 9,192) and male parent 'Red Williams' (not patented). 'NC4' was selected and first asexually propagated by budding 2008, and has been observed to remain true to type over successive asexually propagated generations. The original cross, selection and subsequent asexual propagation of the new variety were carried out at Staplehurst, Tonbridge, Kent, United Kingdom.

'NC4' is distinguished by its fruit, the skin color of which is red-purple at harvest, turning to red-orange upon ripening. Comparisons of 'NC4' to its parents and similar variety 'Sweet Sensation' (not patented) are set forth in the following tables.

TABLE 1

Comparison of 'NC4' to 'Concorde'

| Characteristic | 'NC4' | 'Concorde' |
|---|---|---|
| Fruit skin color after storage | Red-orange | Green-yellow |
| Fruit maturity | Later | Earlier |
| Aroma | More aromatic | Less aromatic |
| Branch thickness | Thinner | Thicker |
| Leaf color | Darker | Lighter |

TABLE 2

Comparison of 'NC4' to 'Red Williams'

| Characteristic | 'NC4' | 'Red Williams' |
|---|---|---|
| Fruit maturity | Later | Earlier |
| Storage ability | Longer | Shorter |
| Fruit Shape | Elongated | Intermediate |
| Russet at stem end | More russet | Less russet |
| Bloom time | Later | Earlier |

TABLE 3

Comparison of 'NC4' to 'Sweet Sensation'

| Characteristic | 'NC4' | 'Sweet Sensation' |
|---|---|---|
| Russet at stem end | More russet | Less russet |
| Fruit Shape | Elongated | Short to intermediate |
| Area of overcolor | More overcolor | Less overcolor |
| Flavor | Similar to 'Red Williams' | Similar to 'Comice' (not patented) |
| Fruit Maturity | Later | Earlier |

BRIEF DESCRIPTION OF THE PHOTOGRAPHS

Figure 1:
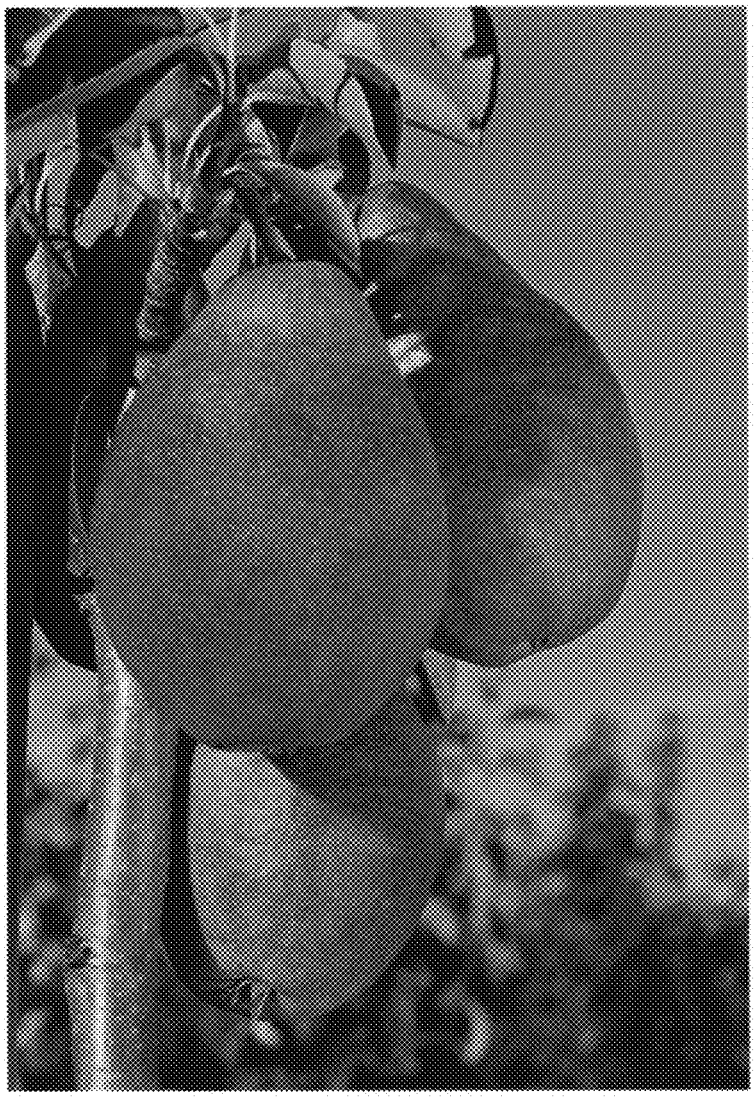
Figure 2:
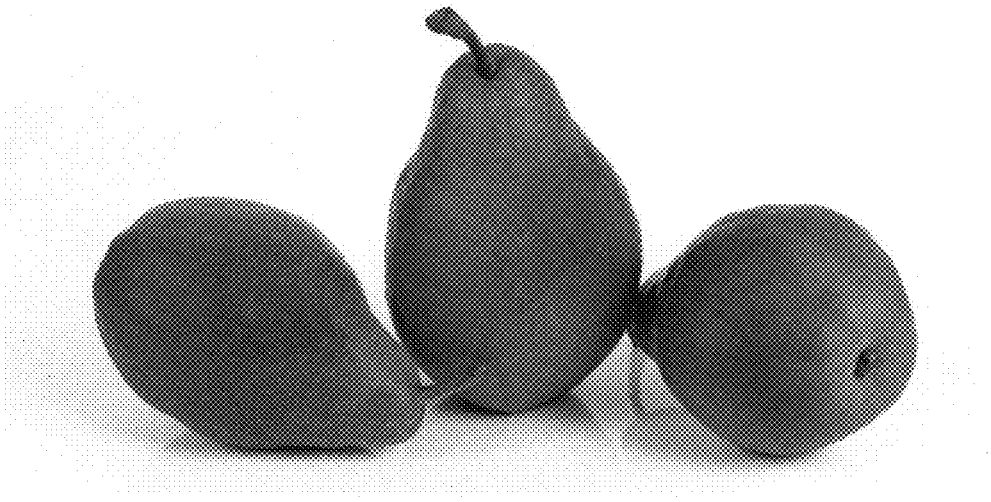
Figure 3:
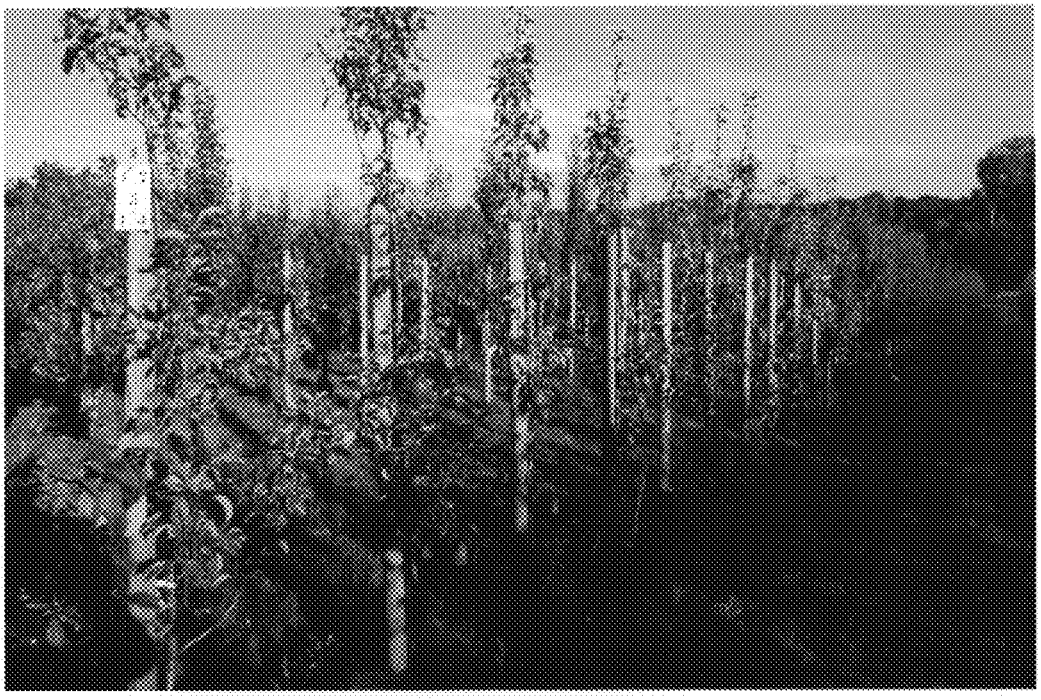
Figure 4:
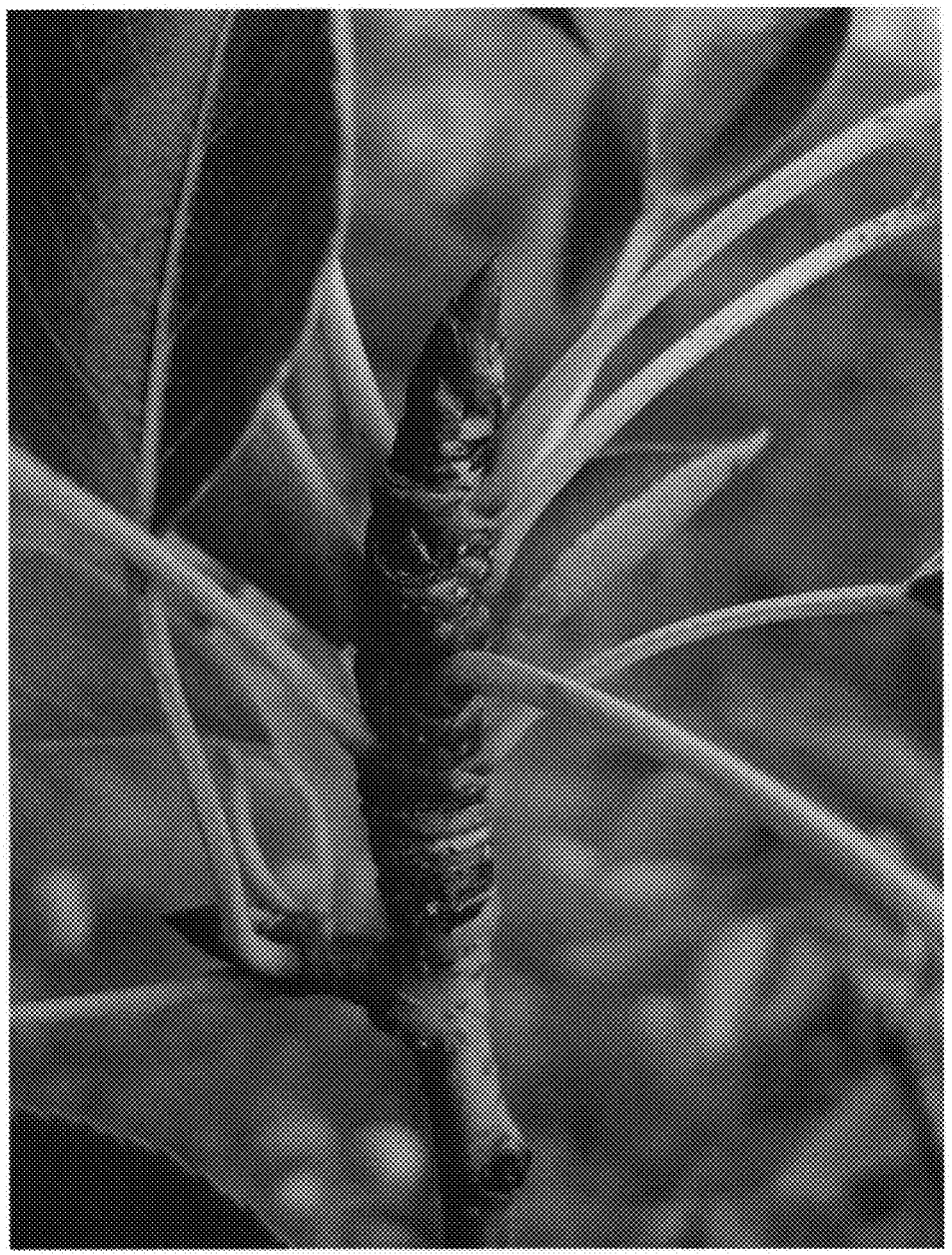
Figure 5:
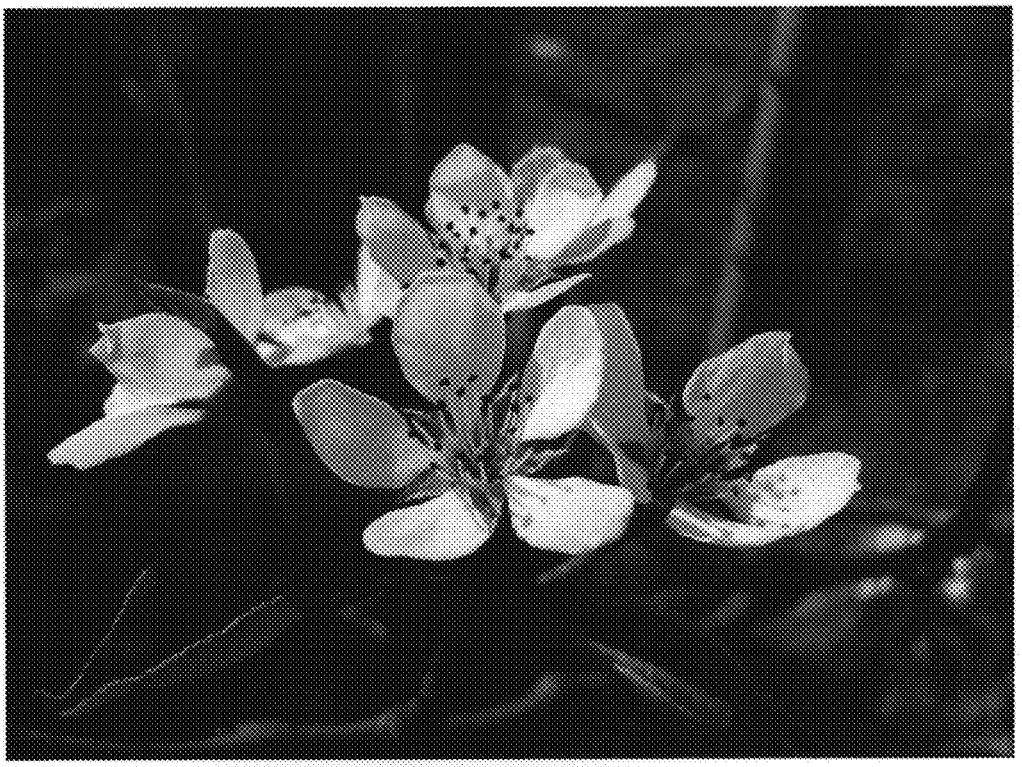
Figure 6:
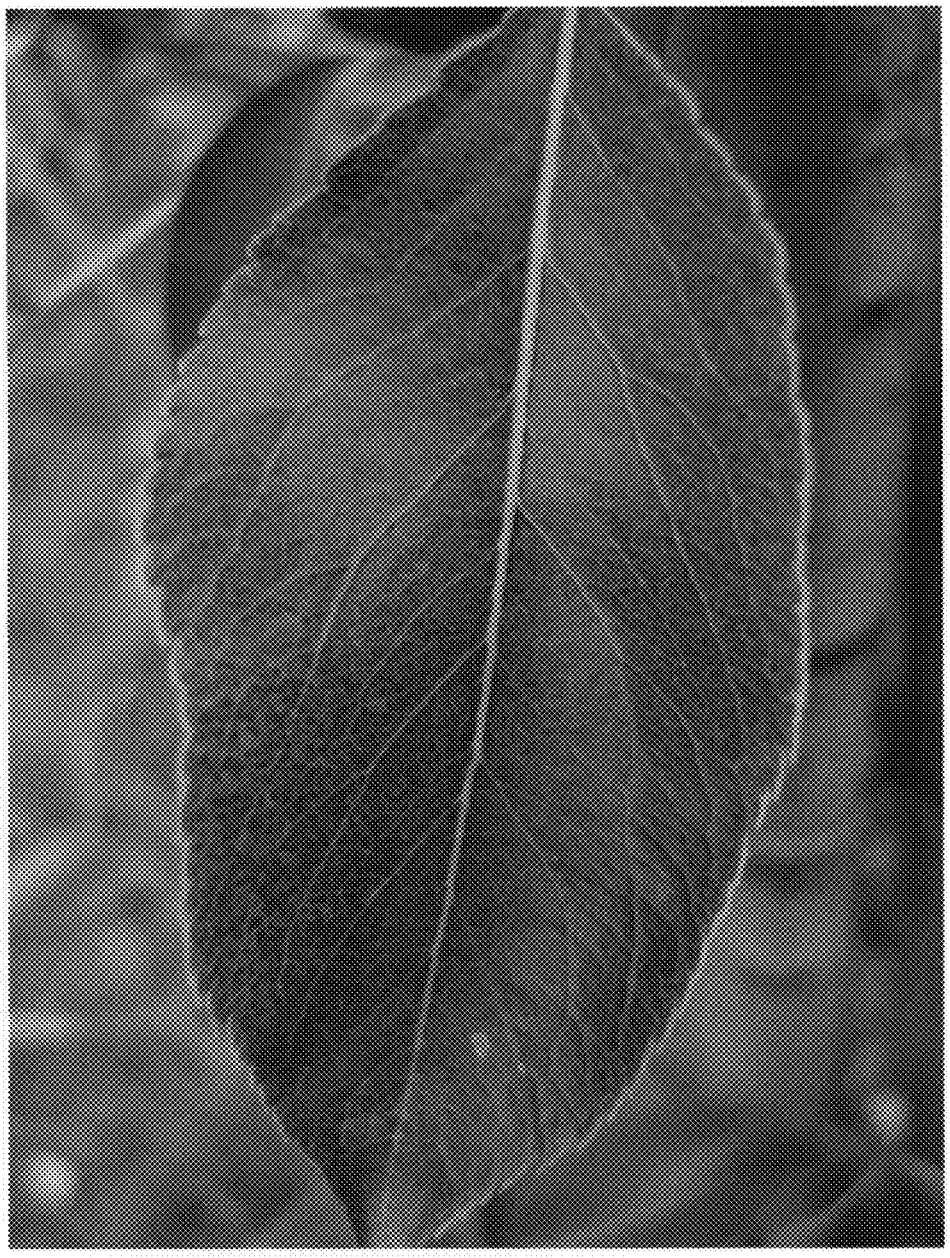
Figure 7:
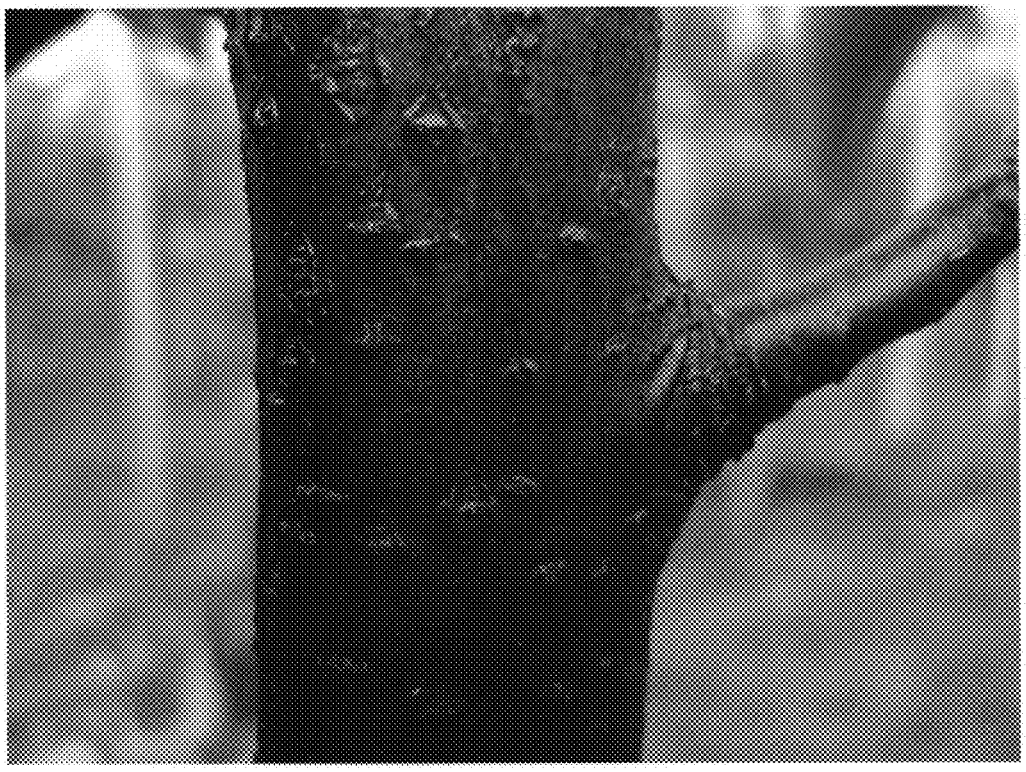
Figure 8:
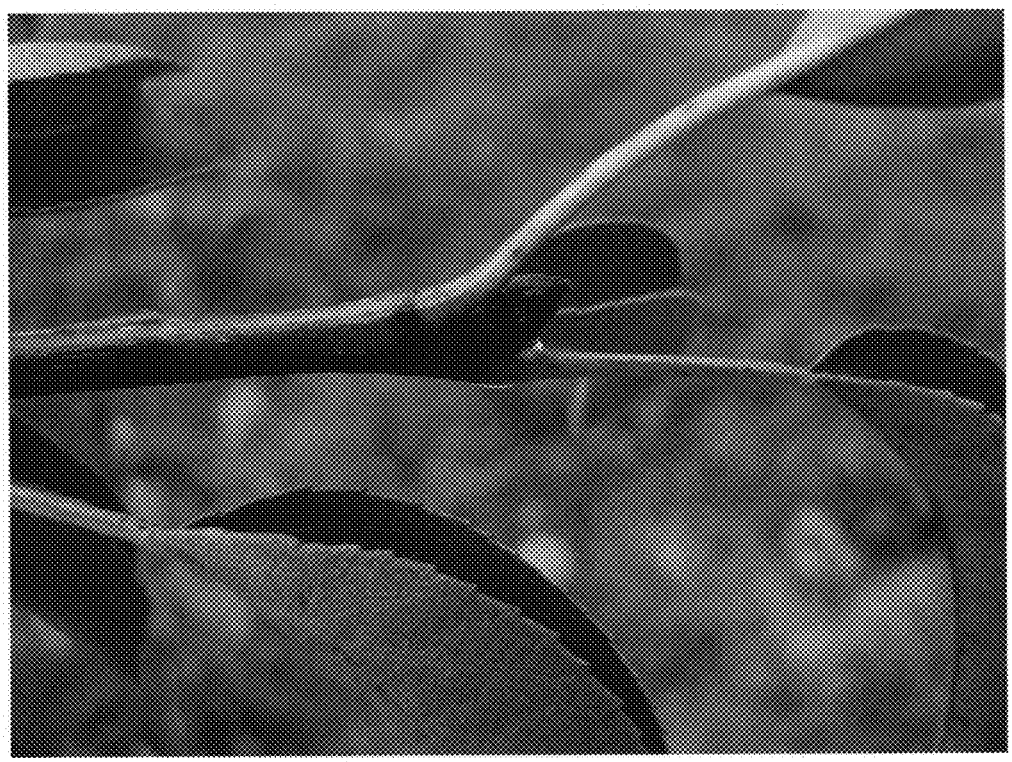

FIGS. 1 and 2 show the fruit of 'NC4';
FIG. 3 shows trees and fruit of 'NC4';
FIG. 4 shows a flower bud of 'NC4';
FIG. 5 shows blossoms of 'NC4';
FIG. 6 shows a leaf of 'NC4';
FIG. 7 shows the trunk of 'NC4'; and
FIG. 8 shows a vegetative bud of 'NC4'.

BOTANICAL DESCRIPTION OF THE VARIETY

The following botanical description is based on observations made during the 2016 and 2017 growing seasons at Seiches sur le Loir, France of two- and three-year-old trees grown on 'SYDO' rootstock (not patented). All colors are described according to The Royal Horticultural Society Mini Colour Chart (2005). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Weak.
- *Type*.—Half-spur.
- *Habit*.—Fastigiate.
- *Height*.—3 m.
- *Spread*.—1.2 m.
- *Trunk diameter* (*at* 30 *cm above the graft*).—26 mm.
- *Bark texture*.—Smooth with lenticels.
- *Bark color*.—Grey N200C.
- *Trunk lenticels*.—Length 2 mm, width 1 mm; color yellow brown N167A; density about 3 per $cm^2$.
- *Winter hardiness*.—Moderate.

Branch (fruiting branches located at about 1 m above the graft union):
- *Length*.—30 cm.
- *Diameter*.—9 mm.
- *Crotch angle*.—80°.
- *Bark color*.—Grey N200C.
- *Texture*.—Rough.

One year old shoot:
- *Length*.—28 cm.
- *Color*.—Dark Brown 200B.
- *Pubescence*.—Absent.
- *Thickness*.—7 mm.
- *Internode length*.—21 mm.
- *Shoot lenticels*.—Round, diameter 1.5 mm; color light yellow brown 163B; density about 9 per $cm^2$.
- *Vegetative bud shape*.—Pointed.
- *Vegetative bud color*.—Dark brown 200B.
- *Position of buds in relation to shoot*.—Adjoined.

Flower buds:
- *Quantity per spur*.—1 to 10.
- *Shape*.—Swollen and pointed.
- *Length*.—9 mm.
- *Diameter*.—5 mm.
- *Color*.—Dark brown 200B and orange brown 166C.

Flowers:
- *Diameter of fully open flower*.—27 mm.
- *Depth of open flower*.—6 mm.
- *Relative position of petal margin*.—Not touching.
- *Number per cluster*.—6.
- *Date of first bloom*.—'Conference' (not patented)+1 day (Mar. 29, 2017).
- *Date of full bloom*.—Same as 'Conference' (Mar. 30, 2017).
- *Pollination requirement*.—Pollenizer required, such as 'Conference', 'Rocha' (not patented), 'Guyot' (not patented).

Petals:
- *Number per flower*.—5.
- *Shape*.—Elliptical.
- *Length*.—14 mm.
- *Width*.—9 mm.
- *Apex*.—Obtuse.
- *Base*.—Acute.
- *Margin*.—Smooth.
- *Texture of upper surface*.—Smooth.
- *Texture of lower surface*.—Smooth.
- *Color of upper surface*.—White 155C.
- *Color of lower surface*.—White 155C.

Pistils:
- *Length*.—11 mm.
- *Color*.—Yellow-green 145A.

Stigma:
- *Length*.—1 mm.
- *Color*.—Yellow-green 145A.

Style:
- *Length*.—7 mm.
- *Color*.—Yellow-green 149D.

Ovary:
- *Length*.—3 mm.
- *Color*.—Green 146C.

Anthers:
- *Quantity*.—20.
- *Length*.—7 mm.
- *Presence of pollen*.—Yes.
- *Color of pollen*.—Light yellow 8C.

Pedicel:
- *Length*.—22 mm.
- *Diameter*.—1 mm.
- *Color*.—Purple brown 183A.

Sepals:
- *Quantity*.—5.
- *Color*.—Brown 199A and yellow-green 145A.
- *Length*.—6 mm.
- *Width*.—2 mm.
- *Shape*.—Pointed.
- *Apex*.—Acute.
- *Margin*.—Smooth.
- *Attitude in relation to corolla*.—Touching.

Leaves:
- *Shape*.—Elliptical.
- *Length*.—62 mm.
- *Width*.—42 mm.
- *Blade margin*.—Bluntly serrate.
- *Apex*.—Right angled with a tip.
- *Base shape*.—Obtuse.
- *Color of upper surface*.—Green 136A.
- *Color of lower surface*.—RHS 137C.
- *Attitude in relation to shoot*.—Outward.

Petiole:
- *Length*.—37 mm.
- *Diameter*.—1 mm.
- *Color*.—Yellow-green 145A.
- *Stipule color*.—Yellow-green 145A.
- *Stipule shape*.—Pointed and stretched.
- *Stipule length*.—12 mm.
- *Stipule width*.—0.5 mm.
- *Stipule apex*.—Pointed.

Fruit:
- *Quantity per cluster*.—2 to 4.
- *Height*.—98 mm.
- *Width*.—71 mm.
- *Weight*.—213 g.
- *General shape in profile*.—Pyriform, elongated.

*Position of maximum diameter*.—Slightly towards calyx.
*Symmetry in longitudinal section*.—Moderate to high.
*Profile of sides*.—Concave.
*Skin texture*.—Slightly rough.
*Skin ground color at harvest*.—Yellow green 145C.
*Skin over color at harvest*.—Purple 71A.
*Skin ground color after storage*.—Yellow brown 163A.
*Skin over color after storage*.—Orange red 41B and red 47A.
*Area of over color of skin*.—Medium to large (50% to 80%).
*Intensity of over color of skin*.—Medium.
*Relative area of russet around eye basin*.—Moderate.
*Relative area of russet on cheeks*.—Weak to moderate.
*Relative area of russet on stalk attachment*.—High.
*Length of stalk*.—22 mm.
*Thickness of stalk*.—3 mm.
*Curvature of stalk*.—Moderate.
*Attitude of stalk in relation to axis of fruit*.—Slightly angled.
*Stalk color*.—Dark brown 165A.
*Depth of eye basin*.—5 mm.
*Width of eye basin*.—16 mm.
*Attitude of sepals at harvest*.—Dry.
*Firmness of flesh*.—Quite firm at harvest, 7 kg/0.5 $cm^2$.
*Flesh texture*.—Smooth.
*Aroma*.—Similar to 'Red Williams'.
*Juiciness*.—Average to High.
*Brix*.—12.5 ° Brix.
*Flesh coloration*.—White 155B.

Seeds:
*Quantity per fruit*.—6 to 8.
*Shape*.—Oval-oblong.
*Length*.—10 mm.
*Width*.—5 mm.
*Color*.—Dark brown 200C and yellow brown N167A.

Harvest:
*Time for harvest*.—Early October (about 3 weeks after 'Conference').
*Time of maturity for consumption*.—November to March.
*Amount of fruit produced per tree per harvest*.—About 30 (3rd leaf).

Market use: Fresh fruit, table fruit.
Storage characteristics: Cold store around 0° C.

I claim:

1. A new and distinct Pear tree substantially as described and illustrated herein.

* * * * *